United States Patent [19]

Lucas et al.

[11] Patent Number: 4,824,249
[45] Date of Patent: Apr. 25, 1989

[54] SYSTEMS FOR THE DIRECT ANALYSIS OF SOLID SAMPLES BY ATOMIC EMISSION SPECTROSCOPY

[75] Inventors: Michael A. Lucas, Ivanhoe; Terry C. Hughes, Carlton North, both of Australia

[73] Assignee: Chamber Ridge Pty. Ltd., Camberwell, Australia

[21] Appl. No.: 165,261

[22] PCT Filed: Apr. 15, 1987

[86] PCT No.: PCT/AU87/00101

§ 371 Date: Dec. 1, 1987

§ 102(e) Date: Dec. 1, 1987

[87] PCT Pub. No.: WO87/06341

PCT Pub. Date: Oct. 22, 1987

[30] Foreign Application Priority Data

Apr. 16, 1986 [AU] Australia .............................. PH05481

[51] Int. Cl.$^4$ ................................................ G01J 3/30
[52] U.S. Cl. ....................................... 356/311; 356/314; 364/498
[58] Field of Search ............... 364/498; 356/311, 312, 356/303, 305, 307, 308; 315/111.01, 111.21, 107, 111.91; 204/192.12, 192.13

[56] References Cited

U.S. PATENT DOCUMENTS

| | | | |
|---|---|---|---|
| 3,601,489 | 8/1971 | Gelder | 356/314 X |
| 3,610,760 | 10/1971 | Lowe | 356/314 X |
| 3,876,305 | 4/1975 | Gough et al. | 356/314 |
| 4,097,781 | 6/1978 | Koizumi et al. | 315/176 |
| 4,128,336 | 12/1978 | Butler | 356/314 X |
| 4,366,418 | 12/1982 | Mayama et al. | 356/314 X |
| 4,462,685 | 7/1984 | Smith, Jr. et al. | 356/307 |

FOREIGN PATENT DOCUMENTS

0025601 6/1979 Australia .

OTHER PUBLICATIONS

Applied Spectroscopy, vol. 32, No. 3, 1978, T. C. Wolfe et al; "Optimization of Pulsing Conditions for Hollow Cathode Lamps for Atomic Fluorescence Spectrometry", pp. 265–268.

Spectroscopy Letters, vol. 10, No. 9, 1977, pp. 727–736, R. B. Djulgerova, "Spectroscopical Effects Arising under Application of Pulse Supply to Zinc Hollow Cathode Discharge".

Primary Examiner—Eugene R. LaRoche
Assistant Examiner—Seung Ham
Attorney, Agent, or Firm—Albert L. Jeffers

[57] ABSTRACT

An analysis system for directly analyzing solid samples by atomic emission spectroscopy wherein the system includes an atomic spectral lamp (1) of the type which enables a solid sample to be analyzed to be demountably located as a cathode of the lamp (1), means (2) for producing a primary electric discharge by cathodic sputtering from the sample via connection (8) and a secondary boosted discharge for analytical emission via connection (9), spectral wave length analysis device (4) being arranged to receive and determine the intensity of spectral lines emitted by the lamp (1), and control means (3) for controlling the system, the current level of the sample cathode and the operation of the spectral wave length analysis device (4) being controlled on the basis of output from the photomultiplier tube (7) such that the intensity of the spectral lines is maximized and the relationship between spectral line intensity and concentration of the corresponding element in the sample is maintained in a region which is substantially linear.

8 Claims, 8 Drawing Sheets

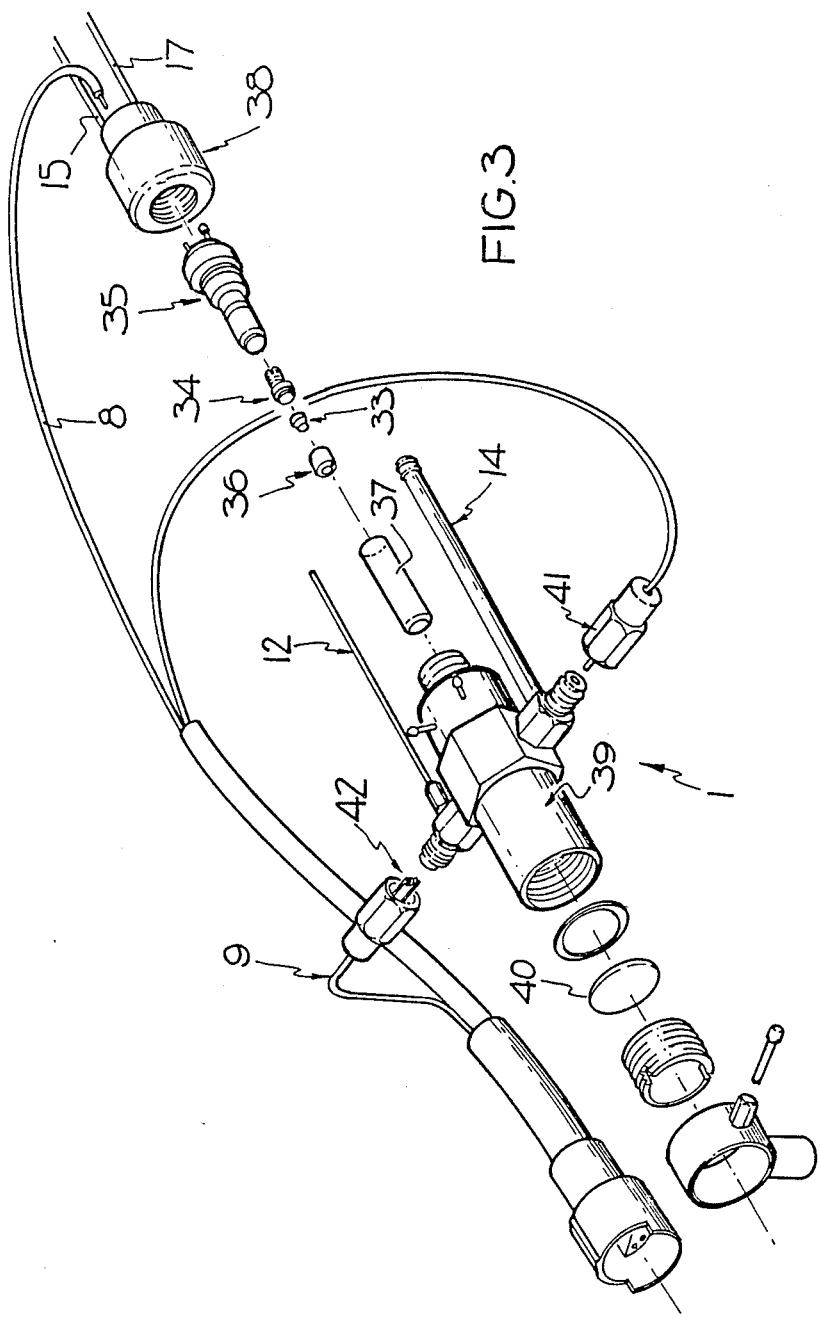

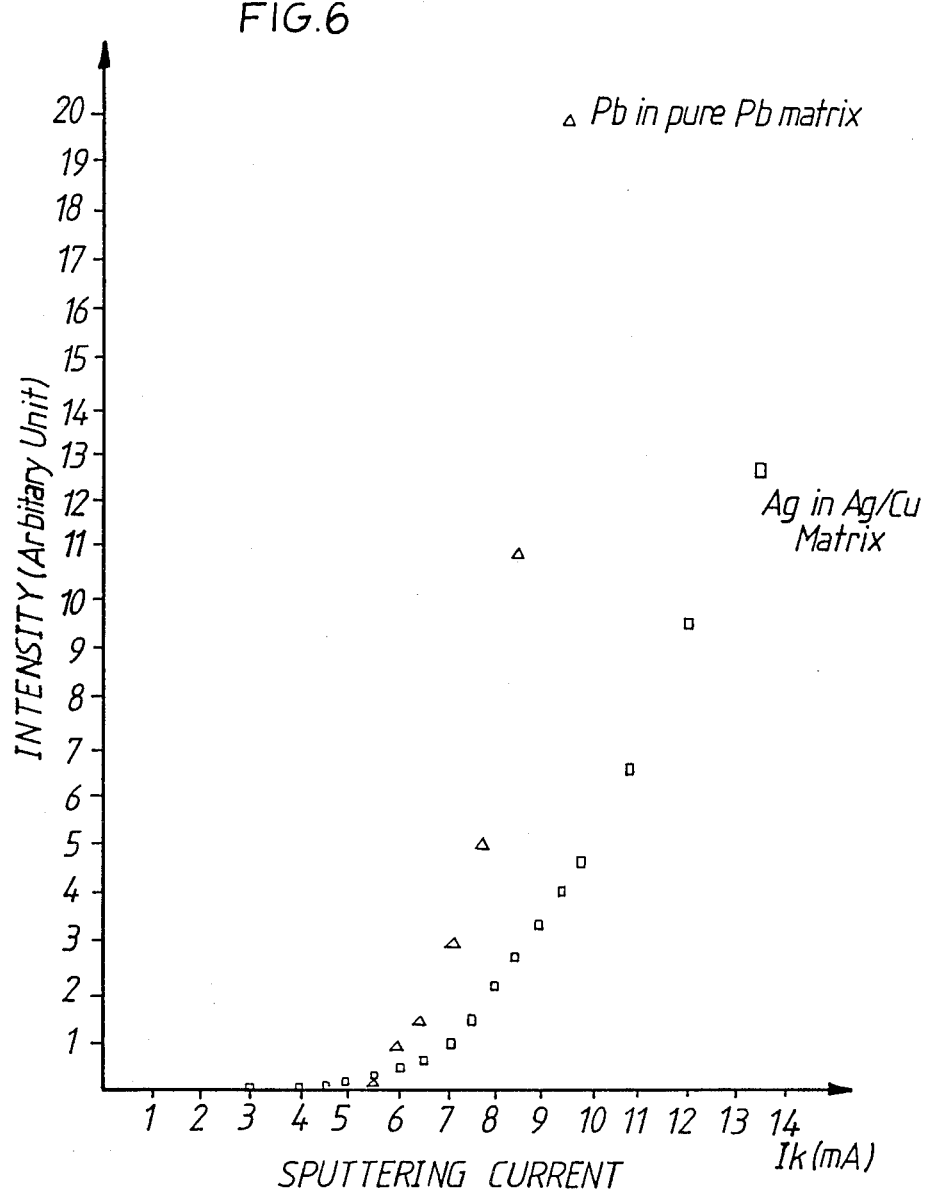

SYSTEMS FOR THE DIRECT ANALYSIS OF SOLID SAMPLES BY ATOMIC EMISSION SPECTROSCOPY

This invention relates to systems for the direct analysis of solid samples by atomic emission spectroscopy.

The use of spectroscopy for the analysis of samples is widely practised using atomic absorption, atomic emission or atomic fluorescence techniques in the spectroscopic analysis of a sample.

The most widely used elemental analysis techniques are atomic emission and atomic absorption and both techniques have well-known advantages and disadvantages. While the atomic absorption technique is relatively inexpensive, using simple instrumentation, performs rapid measurements, can be automated, is accurate and sensitive for many elements, and gives total elemental concentrations, little success has thus far been achieved in multi-elemental analysis, the sample must in most cases be in solution so that the technique is therefore destructive, elemental sensitivities vary from element to element, the technique is subject to sample matrix interference so that samples and standards must be matrix matched for accurate work, if the temperature of the flame is not sufficiently high, molecular spectral interference may occur due to incomplete sample break down, the technique is limited to operation in the visible region which eliminates its application to many electronegative elements and the concentration range covered is small (1 to 2 orders of magnitude) requiring sample dilution which can cause errors.

In the case of the atomic emission technique, the major advantages include: the technique may be is truly multi-elemental and simultaneous in its operation, most elements can be measured using ultra violet-visible optics, a wide range of samples can be handled, concentration ranges of five orders of magnitude can be covered, instrumentation is relatively simple and reliable, the instruments can be automated, analytical sensitivity is high, complete sample break down occurs and interferences are restricted to those caused by spectral resolution limitations, and the technique has sub parts per million sensitivity. On the other hand, the principal disadvantages of the atomic emission technique include the requirement for a thermally and physically stabilised high resolution spectrometer, the requirement for complete sample destruction, the matrix dependence of arc/spark analysis and the inaccuracies introduced thereby, the requirement for complete sample decomposition when using inductively coupled plasma which can be difficult with inert materials, the inability to distinguish between isotopes due to Doppler broadening, and the requirement for a power supply of the order of 10 kW.

The ability to rapidly and inexpensively analyse geological exploration samples is important to mining companies. Similarly, it is most important to mining companies to be able to analyze for isotopic information, particularly in the heavier elements such as lead and uranium. At the present time, the principal technique used is ion mass spectrometry which is time consuming, also involves wet chemistry, and therefore expensive with a maximum throughput of the order of 6 samples per day being common.

It is an object of the present invention to provide a system for the analysis of samples using atomic emission spectroscopy which suffers from fewer of the above described disadvantages, and more specifically, enables rapid and relatively inexpensive isotopic analysis.

Accordingly the present invention provides an analysis system for analysis of samples by atomic emission spectroscopy comprising an atomic spectral lamp adapted to receive a solid sample to be analysed as a cathode of said spectral lamp; means for producing a primary electric discharge by cathodic sputtering from said sample, means for passing an inert gas through said spectral lamp; means for producing a secondary boosted discharge for analytical emission; spectral wave length analysis means arranged to receive and determine intensity of spectral lines emitted from said spectral lamp; and control means including means for controlling cathodic sputtering current used for generating said primary electric discharge from said sample and means for controlling operation of said spectral wave length analysis means, all on the basis of output parameters of said spectral wave length analysis means, whereby the cathodic sputtering current is controlled to maximise intensity of a spectral line of an element under investigation such that the relation between spectral line intensity and concentration of the element in said sample under investigation is maintained in a region which is substantially linear. Preferably the control means also includes means for controlling pressure and/or flow rate of said inert gas through said spectral lamp.

In accordance with a second aspect of the present invention there is provided an atomic emission spectroscopy analysis method comprising locating a solid sample to be analysed as a primary cathode of an atomic spectral lamp; delivering a cathodic sputtering current to said sample for producing a primary electric discharge therefrom while passing an inert gas flow through said spectral lamp across said sample, means for producing a secondary discharge for analytical emission; arranging means for analysing spectral wave lengths to receive and determine intensity of spectral lines emitted from said spectral lamp, and controlling (i) cathodic sputtering current delivered to said sample; and (ii) operation of said spectral wave analysis means, all on the basis of output parameters of said spectral wave length analysis means, such that the relation between spectral line intensity and concentration of an element in the sample under investigation is maintained in a region which is substantially linear.

The spectral lamp employed in the practice of the present invention is preferably of the form described in Australian Pat. Nos. 501,757 and 482,264 to the Commonwealth Scientific and Industrial Research Organization, and more particularly of the type manufactured under licence by S.G.E. Australia. This spectral source has commonly been used for analysis using the atomic absorption technique and although it has been suggested by Lomdahl et al. (Analytica Chimica Acta, 148 [1983] 171-180) that the source may be used in emission spectroscopy, a practical system for achieving this form of analysis on a reproducable basis was not until the present invention achieved.

The primary advantages of using the boosted demountable cathode lamp in atomic emission spectroscopy according to the present invention include:

1. Solid samples are handled directly so no wet chemistry is required thereby reducing analysis time and reducing introduced sources of error.

2. Only poor electrical conductor require crushing and mixing with a metallic powder so that minimum sample preparation is required.
3. The lamp provides an extremely stable optical output.
4. The operating parameters of the lamp are easy to control using a small computer.
5. Sample analysis throughput is high thereby reducing the unit cost of analysis.
6. Analysis for isotopes may be performed.
7. Linear output is found to occur over four to five orders of magnitude of elemental concentration.
8. The system is relatively insensitive to minor changes in sample matrix composition.
9. Parts per million sensitivity is possible for a wide range of elements.
10. The system is simple to operate and does not consume much power.
11. The system may be made in a portable form which may be of rugged construction, and
12. Enables simultaneous multi-elemental analysis.

The operating parameters of the boosted demountable cathode lamp must be carefully controlled, particularly as defined above, otherwise the use of the lamp in the atomic emission system will not be successful. Similar control of the parameters of the lamp is not required when used for the atomic absorption technique. By controlling the lamp in the manner defined, an extremely stable output is produced and the system has a high degree of general applicability, unlike most atomic absorption systems which can be used for the analysis of only one element.

The lamp is preferably operated under the control of a small computer which controls not only the cathode current to allow control of the amount of material sputtered into the plasma in the required linear relationship with the cathode current but also controls the pressure of the inert gas, such as argon, which is fed to the lamp, the rate of flow of the inert gas and the temperature of the coolant which circulates through the lamp.

The system may be programmed to investigate any desired element of interest and after the sample is loaded into the lamp, a predetermined test sequence is performed under the control of the computer to produce the required results. Where the elements of the sample under test are unknown, the system may be caused to test the sample for a predetermined list of elements to determine the elements that are present and their concentrations.

As mentioned above, the system is capable of performing isotopic analyses for at least some lighter and heavier elements, and more particularly, many elements of interest in the analysis of geological samples. The ability of the system to analyse for isotopes is believed to be due to the fact that the plasma which is formed by the boosted discharge in the lamp is not superheated so that Doppler broadening does not obscure the isotopic differences in wave number for heavier elements.

One preferred embodiment of the invention will now be described with reference to the accompanying drawings in which:

FIG. 3 is an exploded perspective view of a boosted demountable cathode lamp capable of use in the system of the present invention;

FIG. 6 shows the relationship between intensity and sputtering (cathode) current for two elements in different matrices;

Figure 1:
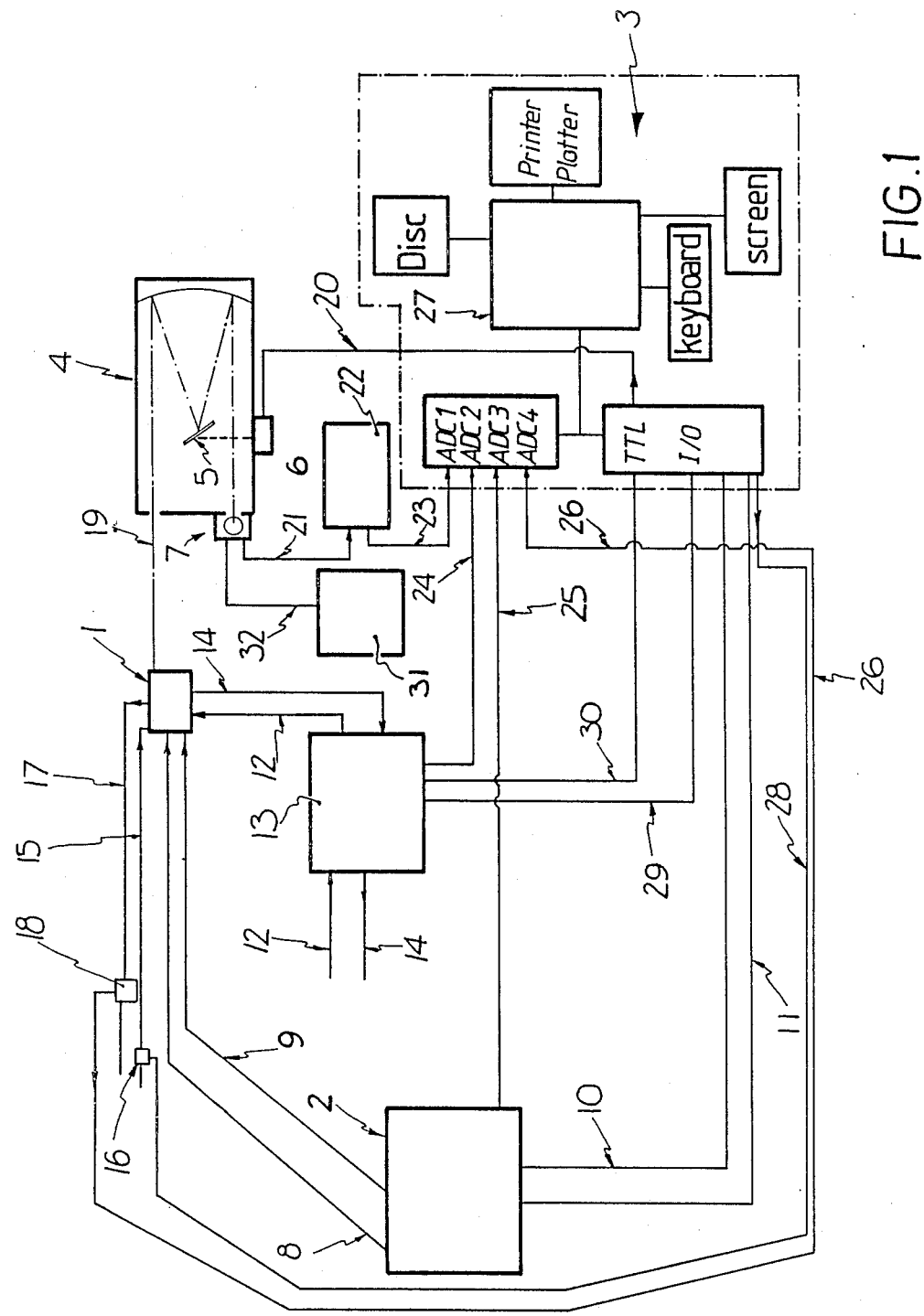
FIG. 1 is a schematic block diagram of the analysis system configured for atomic analysis.

Central to the analysis system is spectral lamp 1 of having a demountable cathode of the general type described in Australian Patent Specification Nos. 482,264 and 501,757 to the Commonwealth Scientific and Industrial Research Organization, and currently manufactured by S.G.E. Australia. The spectral lamp is driven by a suitable power source 2 under the control of a computer system 3. The power supply provides a cathodic sputtering current via connection 8 and a boost current via connection 9. The sputtering current level is controlled in response to signal means via connection 10 from the computer system 3, whereas the boost current is set at a predetermined level and is controlled simply on an on/off basis via connection 11 from the computer system 3. An inert gas such as argon (Ar) is fed to the lamp 1 from a suitable supply (such as a gas bottle) (not shown) via line 12 under the control of a gas pressure sensor 13. A vacuum pump (not shown) is also provided to evacuate the lamp 1 when desired via line 14, and thereby maintain a low pressure in the lamp to allow the flow of argon at low pressure. The spectral lamp 1 may also be provided with a coolant flow into the lamp via line 15 through a flow control valve 16. The coolant flow passing in heat exchange relation with the primary cathode of the lamp to enable temperature control thereof. The coolant is recirculated from the lamp via line 17 and a coolant temperature sensor 18 is provided to sense coolant temperature leaving the lamp 1.

Spectral emissions from the lamp 1 are directed along a light path 19 into spectral wave length analysis equipment 4 which may comprise, in one preferred arrangement, a 1M Czerny Turner 3500 Series Monochromator (A.R.L.) using a suitable defraction grating 5, such as a 4 inch 2400 lines/cm holographic grating, and having entrance and exit slits of suitable dimensions, for example, 20 μm. The defraction grating 5 is mounted on a rotatable table which is rotated by a control motor 6 which is in turn controlled via connection 20 by the computer system 3.

A photomultiplier tube 7 is mounted at the exit slit from the analysis equipment 4 and its output is directed via connection 21 to an amplifier 22 where it is amplified and fed via connection 23 to an analog to digital converter ADC1. A high voltage power supply 31 is provided for the photomultiplier tube 7 via connection 32. Similarly a signal indicative of the argon gas pressure sensor is fed via connection 24 from the gas control pressure sensor 13 to an analog to digital converter ADC2. A signal indicative of sputtering current level to the primary cathode of lamp 1 is delivered via connection 25 to an analog to digital converter ADC3 and a signal indicative of coolant temperature leaving the lamp 1 is delivered via connection 26 to an analog to digital converter ADC4. The outputs of the analog to digital converters are then fed to the computer 27 of the computer system 3. In response to information received by the computer 27 via the analog to digital converters ADC1, ADC2, ADC3 and ADC4, the computer 27 controls the sputtering current level (connection 10), the coolant flow rate by opening or closing the valve 16 via connection 28 and the inert gas pressure or flow rate via connections 29 and 30. Stepping motors (not shown) may preferably be used to control the vacuum pump (also not shown) for creating the flow rate of inert gas through the lamp 1. Similarly stepping motors (not shown) may be used to control the pressure (via a needle valve or the like) of the inert gas directed via line 12 to the lamp 1. The cathodic sputtering current may similarly be controlled by a stepping motor. The foregoing control of cathodic sputtering current, inert gas flow rate and/or pressure and the coolant flow rate is all effected under control of the computer system 3 in response to signals received thereby. The use of stepping motors as aforesaid also leaves open the possibility of manual operation of each of these aspects. The power supplies for the lamp 1 and the photomultiplier tube 7 are all standard control electronics (for example ARL) and need not be further described in the present specification Similarly, the computer 3 may be any suitable micro processor. At the present time, a copam intelligent PC 301-interfaced to the system via a tecmar lab master interface system and under the control of a specially written program has been used with successful results.

The computer 3 controls the cathode current to the lamp 1 as well as the argon gas pressure, and thus flow rate, and the flow rate of cooling water circulating through the lamp 1 whereby the temperature of the lamp is controlled. Control of these parameters is based on the monitored intensity of the spectral line under consideration from the photomultiplier tube 7 and is such that the output intensity of the spectral line and the concentration of the element under investigation is maintained in a region which is substantially linear. By controlling the parameters in this manner, the system ensures that there is not too much of the element under investigation in the plasma created within the lamp and self absorption of the spectral line does not occur. Thus, if the computer detects that the above relationship is not linear, the system can be returned to its desired linear relationship by reducing the cathode current which in turn reduces the amount of material which is being sputtered into the plasma. It is possible to check whether the output is in a desired linear region by following a routine of plotting output intensity against cathode current. For known sample matrices, the shape of this relationship should follow a fitted curve with the intensity increasing as cathode current increases (see FIG. 6) When the relationship is non-linear and self-absorption takes place, the relationship varies from the fit and drops below the fit curve with the output decreasing as cathode current increases. As more analyses are performed, sets of data tables are programmed into the computer 3 and the computer may perform the analysis procedure, to be described further below, automatically.

To prepare a sample for analysis, the sample is formed into a small cylindrical pellet either by cutting and polishing the material itself (if the material is sufficiently conductive) or by crushing the sample into a fine powder and mixing it thoroughly with a conducting binding agent such as copper powder. In general, a mixture containing approximately 50% copper powder is usually satisfactory provided the mixture is thoroughly blended and then made into a pellet by pressing in a die according to a standard procedure.

Figure 3A:
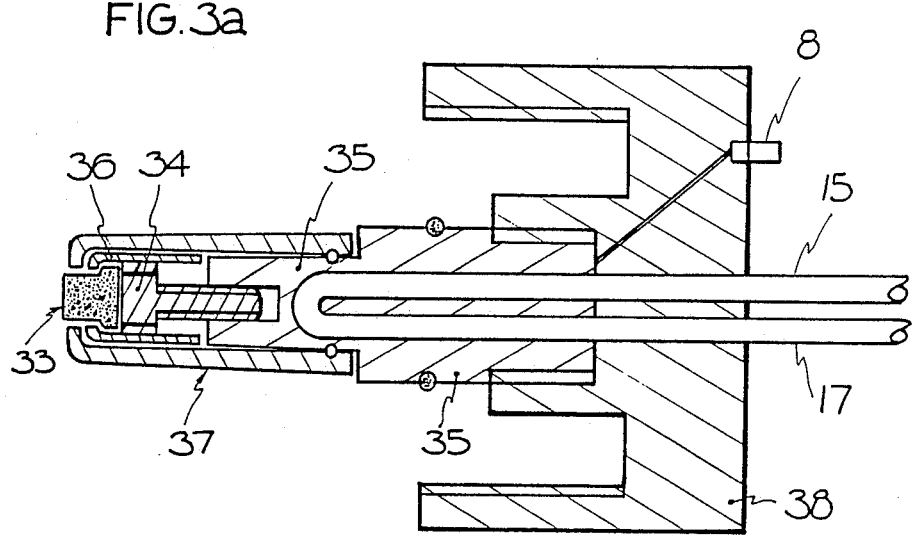
FIG. 3A is an enlarged sketch of a sample holder and "cold finger" which is fitted to the boosted demountable cathode lamp generally shown in FIG. 3.

FIGS. 3 and 3A illustrate details of a suitable demountable cathode spectral lamp 1 for carrying out the present invention. The sample, prepared as aforesaid, forms the primary cathode 33 of the lamp. The sample 33 is positioned on a holder 34 which in turn screws into a cold finger element 35. A sleeve 36 is positioned over the sample 33 and the holder 34 with an insulating sleeve 37 being positioned thereover whereby only the outer end surface of the sample 33 is presented to the internal chamber of the lamp 1. The element 35 screws into an insulating mount member 38 which in turn screws onto the main body 39 of the lamp 1 with the sample operationally positioned therein. A coolant flow circulation is provided via lines 15,17 to flow through the cold finger element 35 to thereby control its temperature as well as the temperature of the sample 33. When the lamp shown in FIG. 3 is assembled the sample 33 is operationally located centrally and optically behind the window 40 which is made from optical quality silica. On either side of the sample 33, there is provided an inert gas introduction pipe 12 and vacuum pipe connection 14 whereby inert gas flow may occur across the sample 33 and the window 40. On one side of the operation chamber an anode 41 is provided and on the other side a secondary cathode in the form of a wound filament 42 is provided. Sputtering cathodic current is supplied via connection B to the sample 33 and boost current is supplied via connection 9 to the secondary cathode 42.

Once the lamp 1 is assembled a "pump down, clean up" cycle is performed under the control of the computer 3. In this cycle, the lamp is evacuated by means of the vacuum pump, the vacuum tap closed to see if the lamp is airtight (if the pressure rises a leak is present), the tap reopened and argon gas introduced into the system at a pressure of approximately 10 Torr to flush any contaminants out of the lamp. Vacuum is once again applied to clear the lamp and the above process is repeated three times. The cathode current is then turned on to clean the surface of the sample and remove any contaminants from the sample. The analysis procedure then begins.

In analysing a sample having known elements, the computer is programmed to include a "shopping list" of elements and proceeds to analyse the sample for each of these elements in turn. For example, for a sample having unknown quantities of Fe, Ni, Cu, and S the sample would be mixed with an Ag powder binding agent and the system would be programmed to set the monochromator for to look at one of the Ag lines, such as 3382.89 Å. The system would set the suitable starting conditions, for example, 2 mA cathode current and 1.5 Torr argon gas pressure. The boost current is then activated to produce boosted glow discharge for approximately sixty seconds to clean the surface of the sample. The computer then increases the cathode current by 0.5 mA and if the intensity of the spectral line detected by the photomultiplier tube 7 increases, the intensity of the output is measured and compared with tables in the computer to estimate if useful amounts of the element are being sputtered off. If not, the computer instructs the stepping motor to increase the cathode current. If a decrease in the output intensity is detected this means that self absorption is taking place and the cathode current is approximately halved and the monitoring procedure proceeds. If useful amounts of the element are being sputtered off, the computer takes the first element (Fe) from the shopping list and sets the monochromator 4 for that element, for example 3737.131 Å, and the output from the photomultiplier tube 7 is monitored against sputtering current to ensure that the element is being sputtered below a level at which self absorption occurs. If the relationship is not linear, as described above, the cathode current is reduced by the computer and the analysis procedures continue. If the output is at a suitable level, the spectral line is scanned to build up statistics to preset levels, the peak is fitted and the computer checks its data store for standards and after correcting for the amount of binder used, places the result in the output file. The computer then proceeds to the next element in the shopping list and the procedure is repeated.

It will be appreciated from the above that the amount of material sputtered into the plasma by different levels of cathode current and gas pressure is totally matrix dependent and accordingly the relationship between the spectral output and the sputtering current, when working in a linear region as described above, is totally matrix dependent. Once a matrix has been characterised by the analysis procedure, the relevant details may be stored in the computer and called up for later comparison.

Where there is no matrix characterisation for comparison, each element in the shopping list is analysed in turn and a plot of spectral output against sputtering current is stored in the computer. Since the material is sputtered away from the sample in proportion to the elements present, all curves should be the same and where a curve starts to differ from the average, self absorption effects must be present and the cathode current must be reduced. Thus, the computer always takes data at a point which is well below any non-linear effects.

Figure 4:
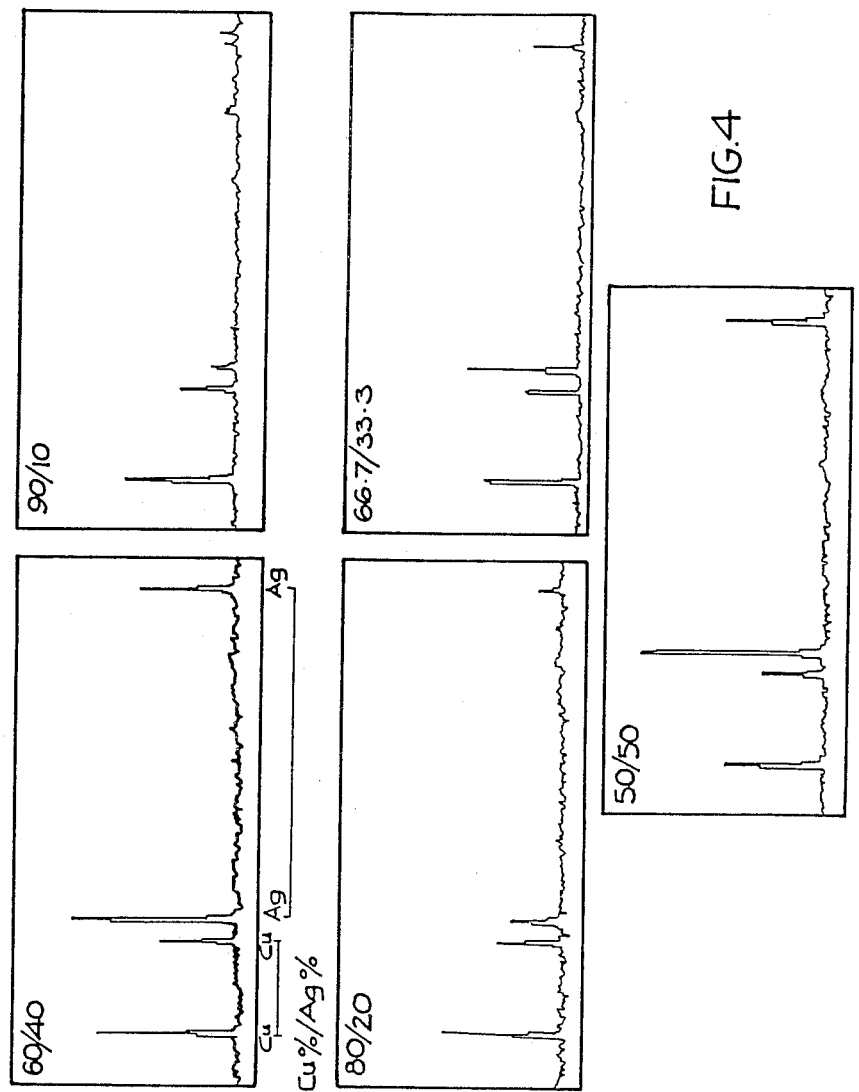
FIG. 4 shows typical data obtained by a system configured according to the invention (using a 3.4M Ebert spectrometer) showing the spectra obtained for different standards at the same conditions, the ratio of copper powder to standard silver being as indicated in each case.
Figure 5:
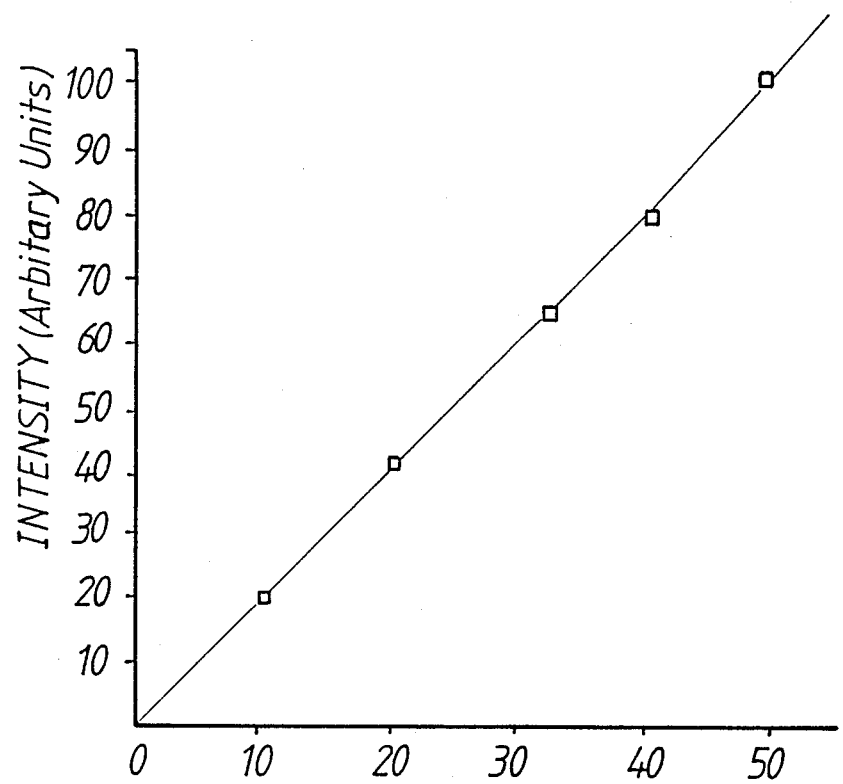
FIG. 5 shows the desired linear relationship between intensity and sample concentration for one specific analytical line.

Typical spectra produced by analysis by a system according to the invention, using a 3.4M Ebert spectrometer and an Apple IIC computer, ar shown in FIG. 4 of the drawings. It will be noted from these spectra that copper becomes strongly self-absorbing above 60%. All data was taken at a cathode current of 8 mA, argon pressure of photomultiplier tube voltage of 1100V, 40 microns entrance slit and 75 microns exit slit.

Where the sample is totally unknown, after the preliminary procedure described above, the monochromator is set at about 3,000 Å and a scan procedure is commenced to build up a plot of output intensity against wave length from which spectral lines identifying the elements present in the sample may be extracted. One method of achieving this is by locating spectral lines having a signal strength greater than three times the background signal, placing the wave length into a "line file" in the computer and then working through the "line file" comparing the wave lengths of the extracted lines with data tables to ascertain the elements present.

An output file showing the elements in order of increasing atomic weight is then created and a decision is made as to what elements in the sample should be more completely analysed according to the procedure described above.

Figure 2:
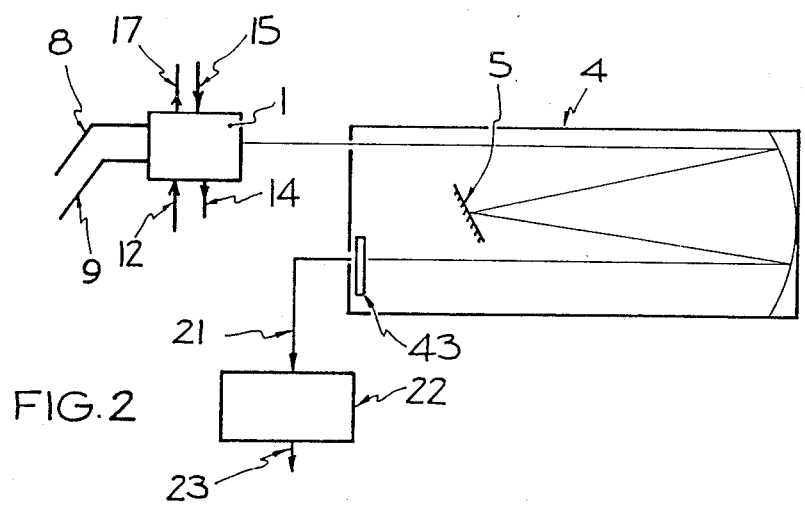
FIG. 2 is a schematic diagram showing the principal changes in the system of FIG. 1 for isotopic analysis.

In the case of isotopic analysis, it is preferred that the system shown in FIG. 1 of the drawings be modified in accordance with FIG. 2 of the drawings. In the arrangement shown in FIG. 2, the monochromator is longer, for example a three to four meter Czerny Turner monochromator having a full width half maximum resolution of the order of 0.0025 Å at 4051 Å, having a large defraction grating and an array detector 43 at the exit. Thus, instead of rotating the grating, the array detector 43 is simply scanned to ascertain the intensity of each spectral line. Once again, it is most important to control the system to ensure that it is operating in a "linear" region in exactly the same as for the atomic analysis procedure described above. It should also be noted that self-absorption will also increase the full width half maximum resolution of a peak, so it is possible to watch the full width half maximum resolution with increasing cathode current to detect when self-absorption starts to occur.

Figure 7:
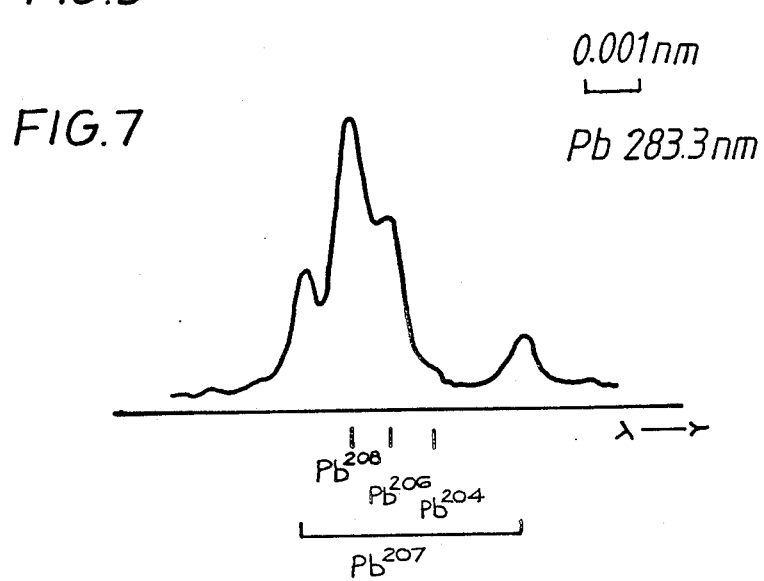
FIG. 7 shows an early experimental result for an isotopic analysis.

It should be appreciated that while the above arrangement is preferred, isotopic analysis may also be performed using the system described in connection with FIG. 1 of the drawings. The important point is that the system according to the present invention is the only emission system which is capable of being used for isotopic analysis of heavy elements. This is believed to be due to the fact that the plasma produced by the boosted demountable cathode lamp is not super heated, due to the continual flow of argon through the lamp and the controlled cooling of the lamp, thereby preventing Doppler broadening which causes merging of the isotopic optical peaks which in turn means that the isotopic information is totally lost. The absence of any Doppler broadening and the ability of this system to achieve isotopic analysis is clearly shown in FIG. 7 of the drawings in which the various isotopes of the lead sample under analysis may be clearly seen.

Figure 8:
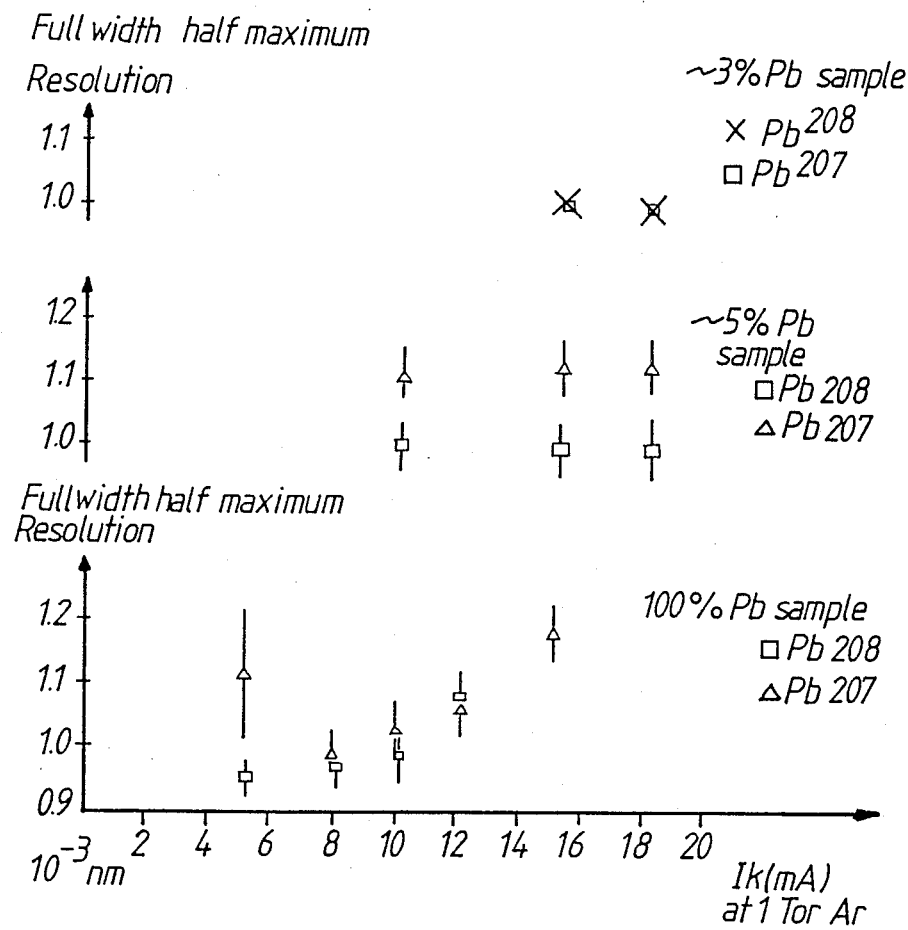
FIG. 8 shows that changes in the cathode current have no effect on full width half maximum resolution.
Figure 9:
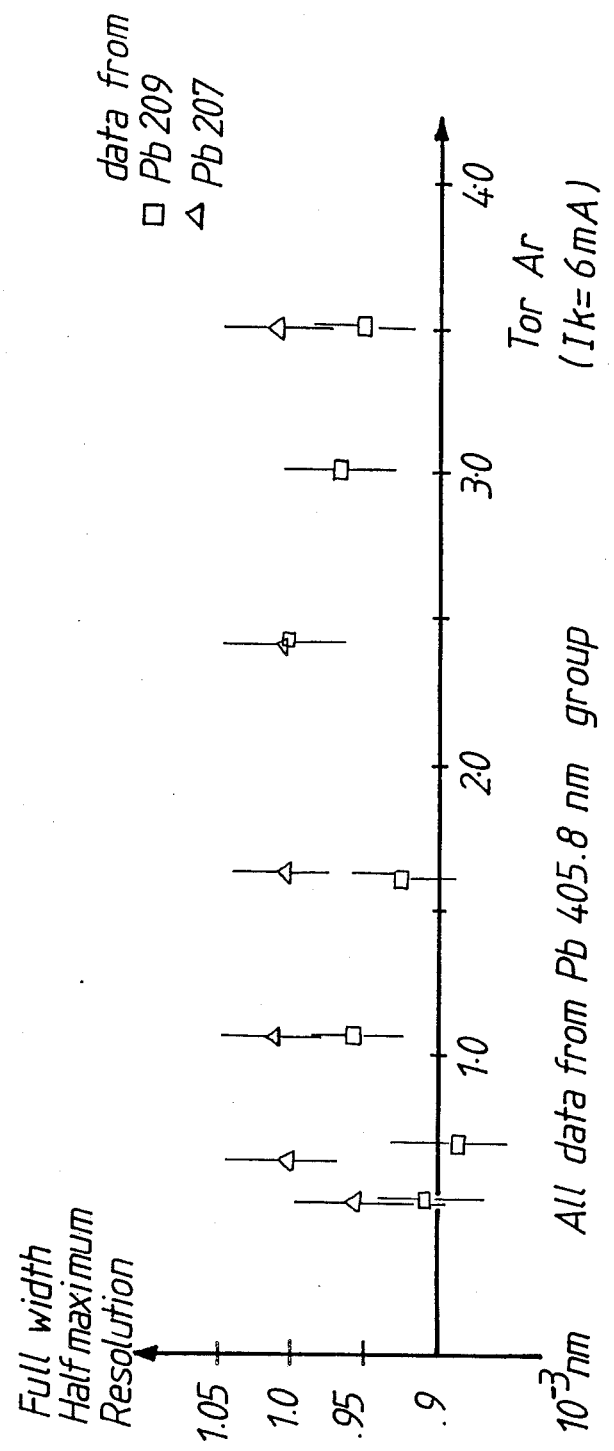
FIG. 9 shows the lack of effect on resolution due to changes in the pressure of the inert gas supplied to the lamp.

The experimental data shown in FIGS. 8 and 9 of the drawings indicate that:
(a) Changes in cathode current have no effect on the full width half maximum resolution for low concentrations of sample (FIG. 8).
(b) For a high concentration sample (100%) the relationship is non-linear due solely to self absorption of the sample, which confirms that full width half maximum resolution may be used to test for self-absorption (FIG. 8).
(c) Changes in the pressure of the argon gas has little effect on the resolution obtained and useful isotopic data may still be obtained (FIG. 9).

While two preferred embodiments of the invention have been described above, it should be appreciated that a multiplicity of combinations of monochromator, grating and computer control may be used to achieve suitable results. In each case, the system provides the principal advantage that solid samples may be analysed in a direct manner for elements and isotopes without the use of wet chemistry. The system is also dynamic in that data is continually being gathered and updated so that the measurements taken may be analysed against previously gathered data to give totally reproducable results.

It will be noted that the above description of typical analysis procedures is not complete in every detail.

Aspects of the procedure which are standard have not been described since they are already well known to persons skilled in the art.

Modifications and adaptations may be made to the above described without departing from the spirit and scope of this invention which includes every novel feature and combination of features disclosed herein.

The claims defining the invention are as follows:

1. An analysis system for analysis of samples by atomic emission spectroscopy comprising an atomic spectral lamp adapted to receive a solid sample to be analysed as a cathode of said spectral lamp; means for producing a primary electric discharge by cathodic sputtering from said sample, means for passing an inert gas through said spectral lamp; means for producing a secondary boosted discharge for analytical emission; spectral wave length analysis means arranged to receive and determine intensity of spectral lines emitted from said spectral lamp; and control means including means for controlling cathodic sputtering current used for generating said primary electric discharge from said sample and means for controlling operation of said spectral wave length analysis means, all on the basis of output parameters of said spectral wave length analysis means, whereby the cathodic sputtering current is controlled to maximise intensity of a spectral line of an element under investigation such that the relation between spectral line intensity and concentration of the element in said sample under investigation is maintained in a region which is substantially linear.

2. An analysis system according to claim 1 wherein said control means also includes means for controlling pressure and/or flow rate of said inert gas through said spectral lamp.

3. An analysis system according to claim 2 wherein the spectral wave analysis means comprises a monochromator.

4. An analysis system according to any one of claims 1 to 3 wherein the spectral lamp comprises a boosted discharge demountable cathode lamp including means for circulating a coolant through said lamp.

5. An analysis system according to claim 4 wherein said control means includes a computer arranged to control operation of said
   (i) means for controlling cathodic sputtering current;
   (ii) means for controlling pressure and/or flow rate of the inert gas; and
   (iii) rate of flow of said coolant through said lamp.

6. An atomic emission spectroscopy analysis method comprising locating a solid sample to be analysed as a primary cathode of an atomic spectral lamp; delivering a cathodic sputtering current to said sample for producing a primary electric discharge therefrom while passing an inert gas flow through said spectral lamp across said sample, means for producing a secondary discharge for analytical emission; arranging means for analysing spectral wave lengths to receive and determine intensity of spectral lines emitted from said spectral lamp, and controlling (i) cathodic sputtering current delivered to said sample; and (ii) operation of said spectral wave analysis means, all on the basis of output parameters of said spectral wave length analysis means, such that the relation between spectral line intensity and concentration of an element in the sample under investigation is maintained in a region which is substantially linear.

7. A method according to claim 6 wherein the pressure and/or flow rate of said inert gas flowing through said spectral lamp is controlled in response to output parameters of said spectral wave length analysis means.

8. A method according to claim 6 or 7 wherein coolant is circulated through said spectral lamp, the flow rate of said coolant being controlled in response to output parameters of said spectral wave length analysis means.

* * * * *